United States Patent
Fiedler et al.

(10) Patent No.: US 8,393,166 B2
(45) Date of Patent: Mar. 12, 2013

(54) SAMPLE COLLECTOR AND COMPONENTS THEREOF

(75) Inventors: Robert R. Fiedler, Pleasant Dale, NE (US); Frederick A. Nabity, Lincoln, NE (US); Henry L. Walters, Lincoln, NE (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 0 days.

(21) Appl. No.: 13/294,915

(22) Filed: Nov. 11, 2011

(65) Prior Publication Data

US 2012/0285183 A1 Nov. 15, 2012

Related U.S. Application Data

(62) Division of application No. 11/980,261, filed on Oct. 30, 2007, now Pat. No. 8,056,353, which is a division of application No. 11/430,606, filed on May 9, 2006.

(51) Int. Cl.
*F25B 1/00* (2006.01)
(52) U.S. Cl. .............. 62/115; 62/259.2; 62/448
(58) Field of Classification Search .......... 62/115, 62/259.2, 511, 297, 298, 448; 312/116, 117
See application file for complete search history.

(56) References Cited

U.S. PATENT DOCUMENTS

| | | | | | |
|---|---|---|---|---|---|
| 3,927,701 | A | * | 12/1975 | Lederer | 141/98 |
| 4,415,011 | A | * | 11/1983 | Grant | 141/284 |
| 5,168,763 | A | * | 12/1992 | Stewart | 73/863.45 |
| 5,645,114 | A | * | 7/1997 | Bogen et al. | 141/145 |
| 5,915,932 | A | * | 6/1999 | Nabity et al. | 417/477.1 |
| 6,354,345 | B1 | * | 3/2002 | Nabity et al. | 141/284 |
| 6,468,059 | B2 | * | 10/2002 | Haser et al. | 417/477.1 |
| 7,318,461 | B2 | * | 1/2008 | Zeller | 141/284 |
| 7,421,881 | B2 | * | 9/2008 | Nathan et al. | 73/19.09 |
| 7,886,579 | B2 | * | 2/2011 | Zinth et al. | 73/31.05 |

* cited by examiner

*Primary Examiner* — Mohammad Ali
(74) *Attorney, Agent, or Firm* — Suiter Swantz pc llo

(57) ABSTRACT

To provide a protective coat on a refrigerated sample collector for a corrosive environment a unitary frame includes a support unit with condenser and evaporator coils mounted to the support unit and an orifice connecting the condenser and evaporator coils. The evaporator coils, condenser coils and restrictor are powder coated after being connected, whereby an effective seal is provided for the restrictor, condenser coils and evaporator coils after they are assembled to the support. The unitary frame can be easily removed or connected as a unit to the sample collector. A peristaltic pump may be used for drawing at least one sample into the refrigerated sample collector and depositing said sample into at least one sample bottle. The peristaltic pump may include contoured tube guides to reduce movement of the peristaltic pump as a roller paddle rotates.

3 Claims, 14 Drawing Sheets

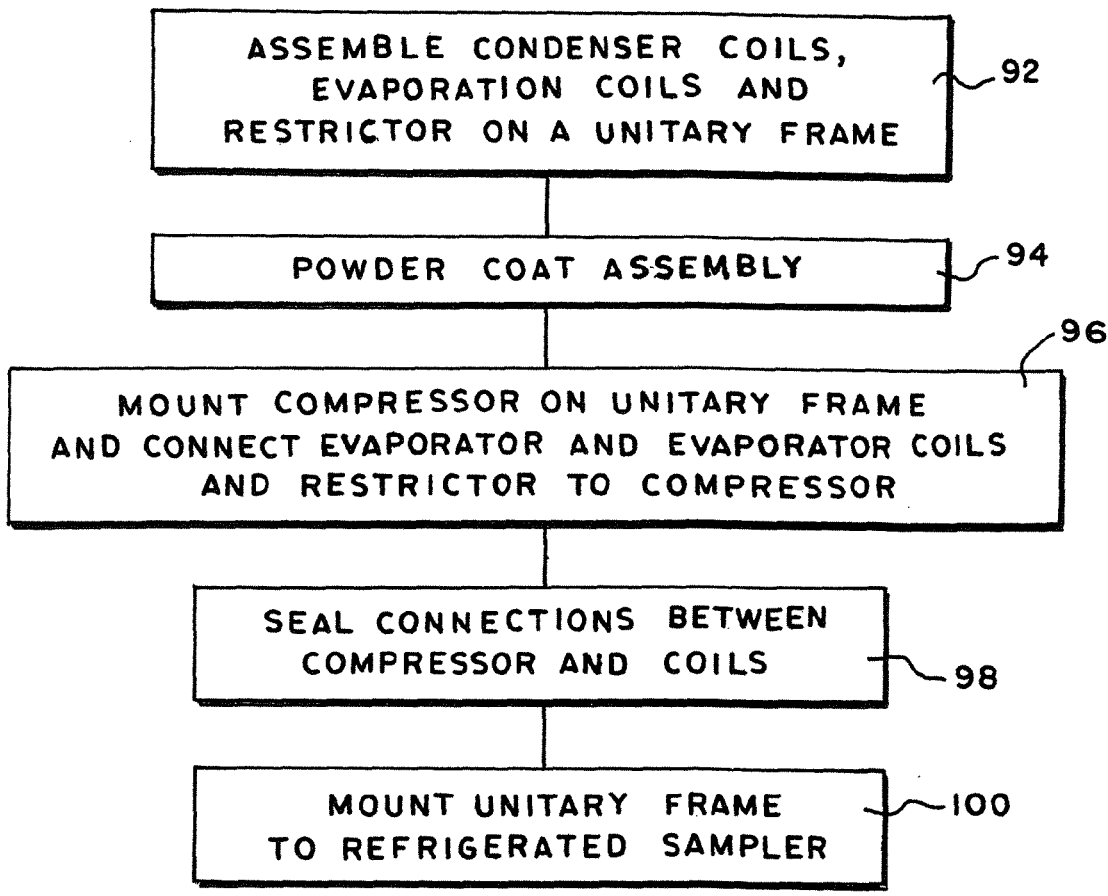
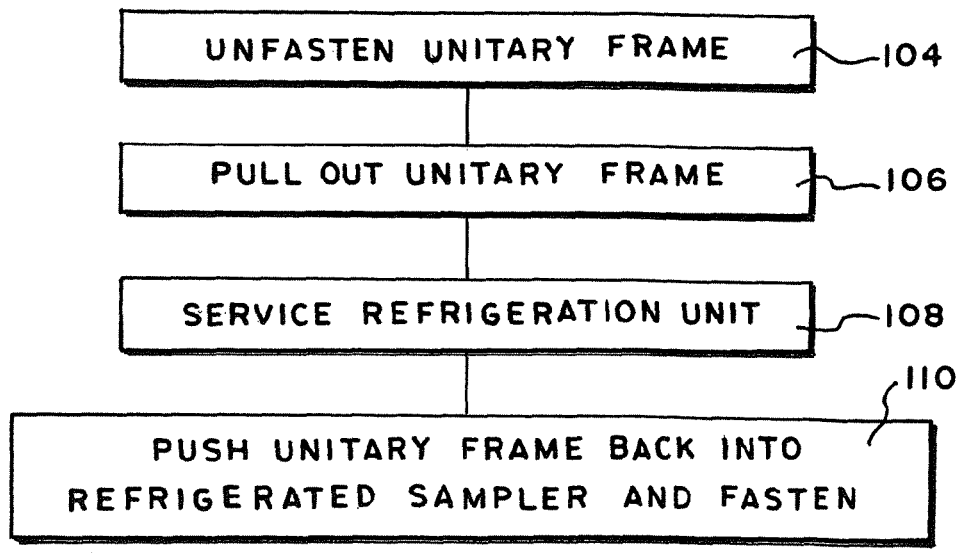

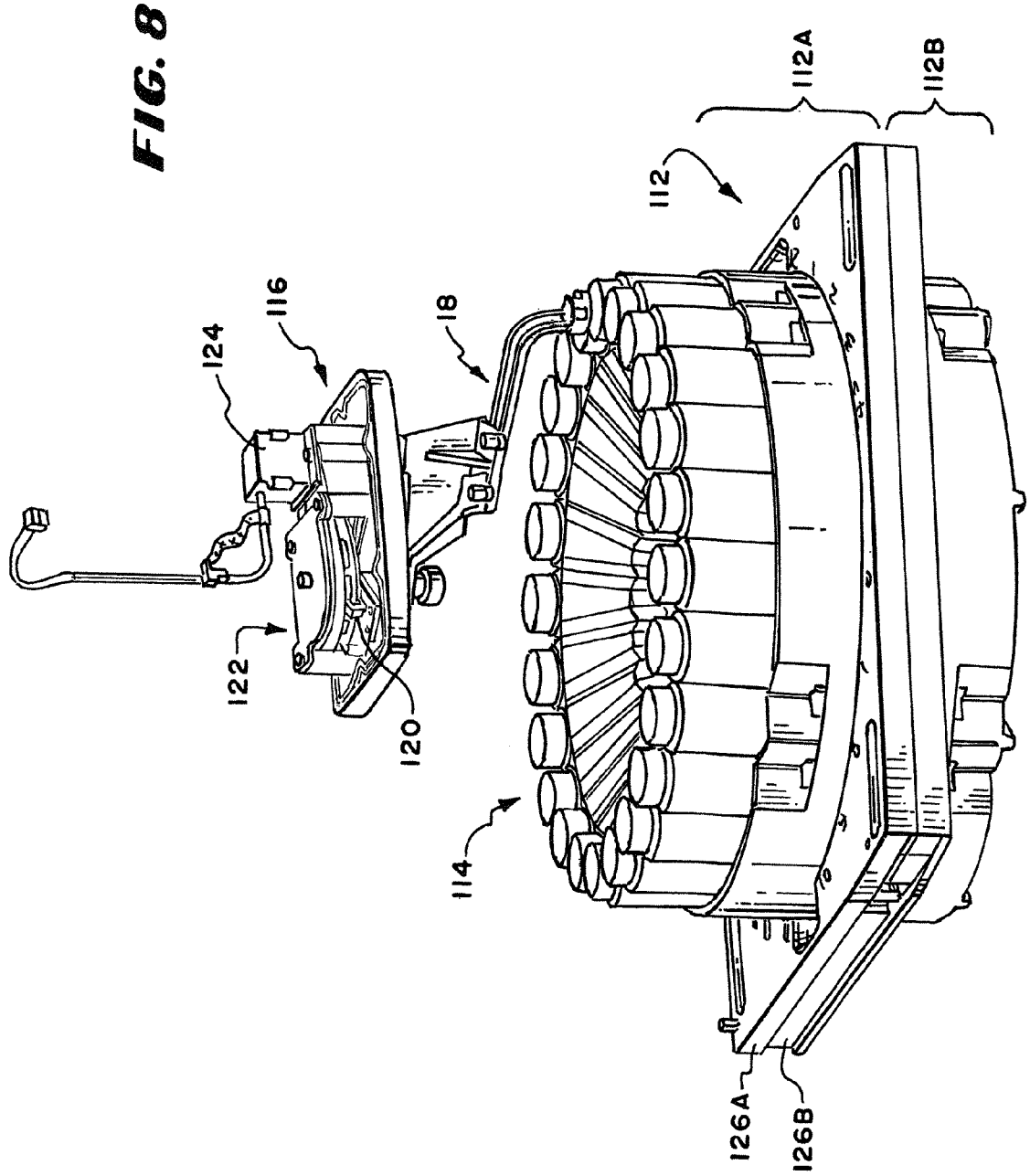

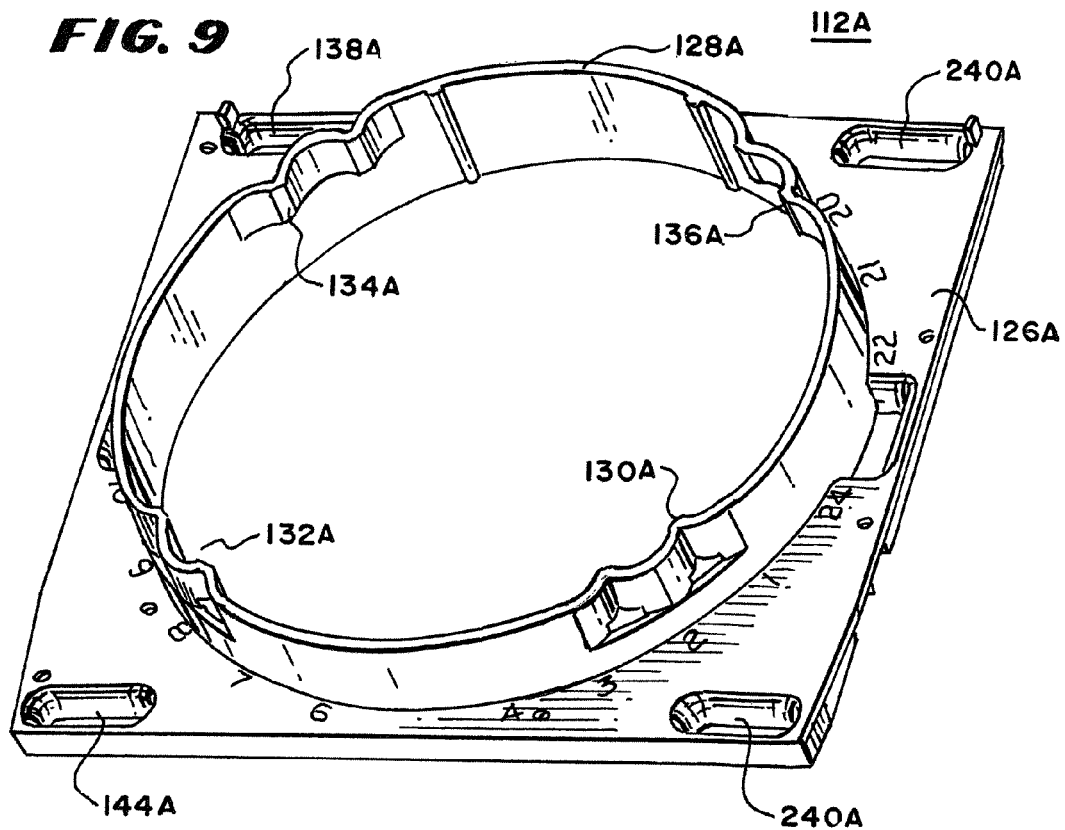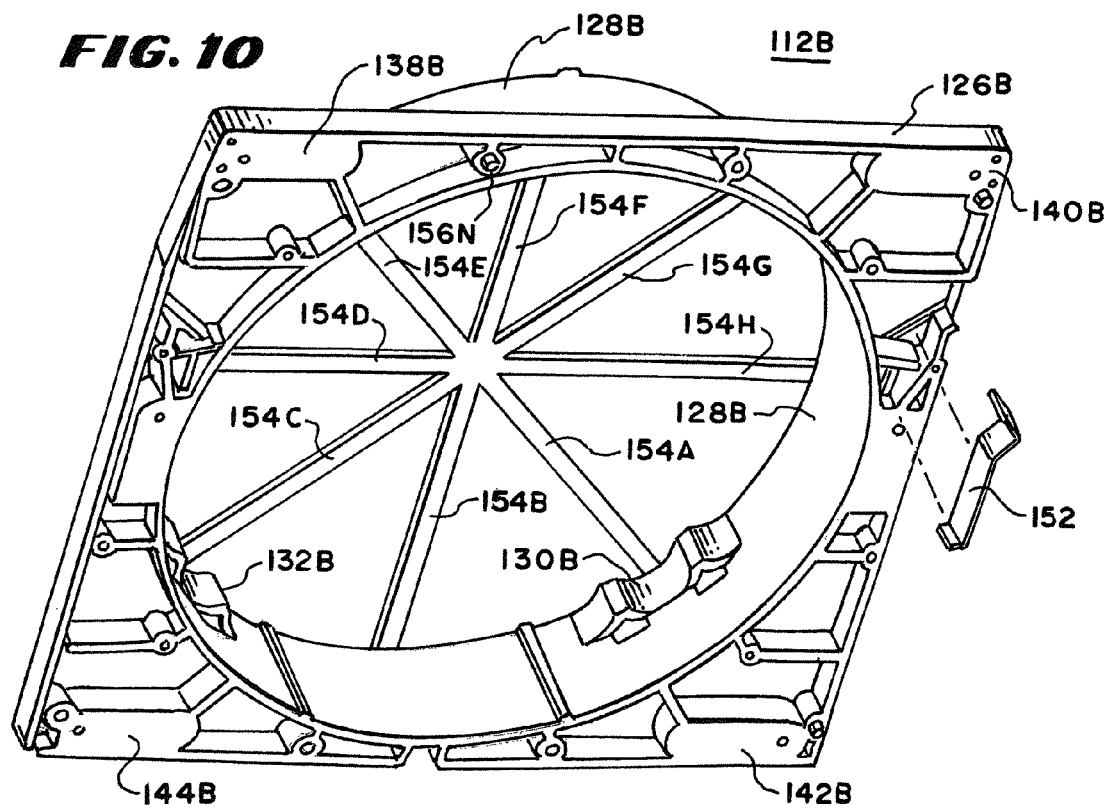

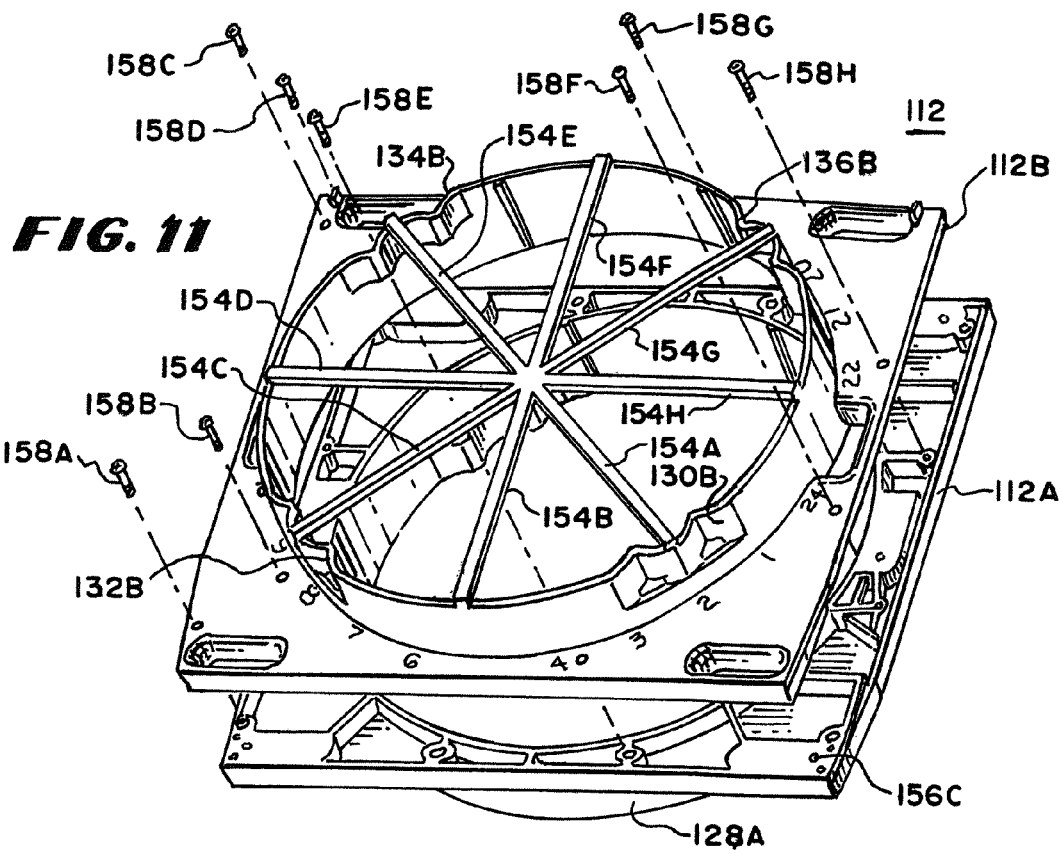
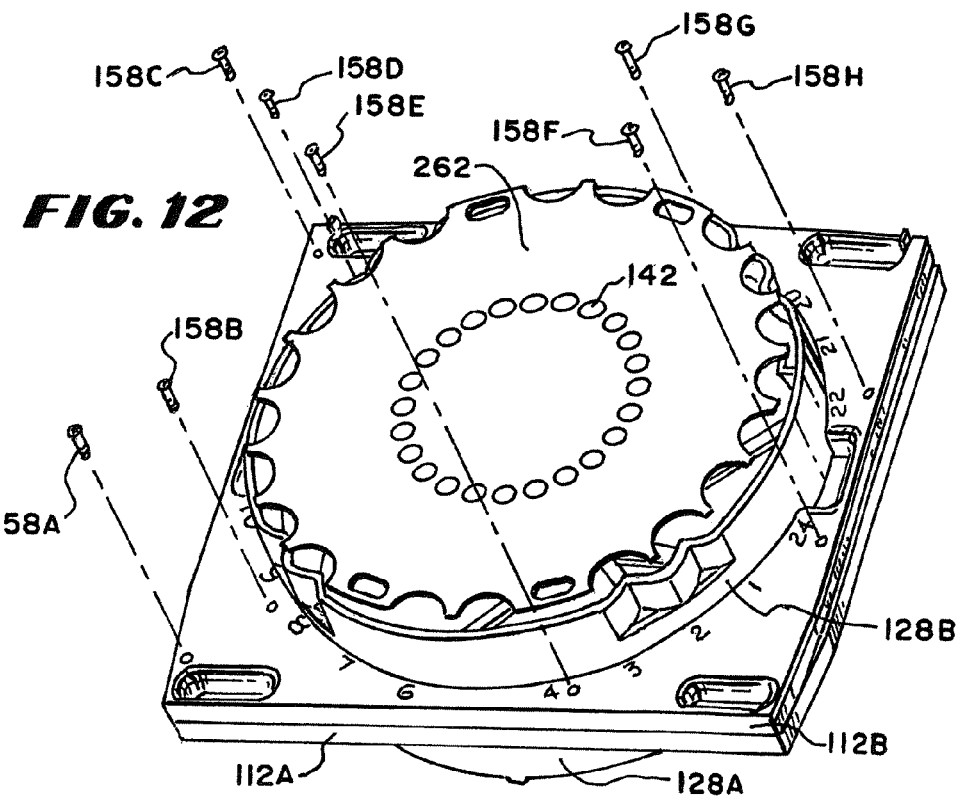

FIG. 13

| 164 |
|---|
| 166 PREPARE SINGLE CAVITY MOLD FOR INJECTION MOLDING ONE RACK HALF WITH ONE POSITIONING SURFACE FOR EACH BOTTLE WITH EACH POSITIONING SURFACE TO BE POSITIONED HALF OF A STABILITY DESIGN DISTANCE FROM ONE END OF THE HALF RACK |
| 168 INJECTION MOLD TWO HALF RACKS FOR EACH RACK DESIRED |
| 170 INVERT ONE HALF RACK AND FASTEN IT TO ANOTHER WITH THE ONE END OF EACH IN CONTACT SO THAT AT LEAST ONE STABILIZING MEMBER IS FORMED WITH THE ONE END BEING CENTERED BETWEEN TWO POSITIONING SURFACES |

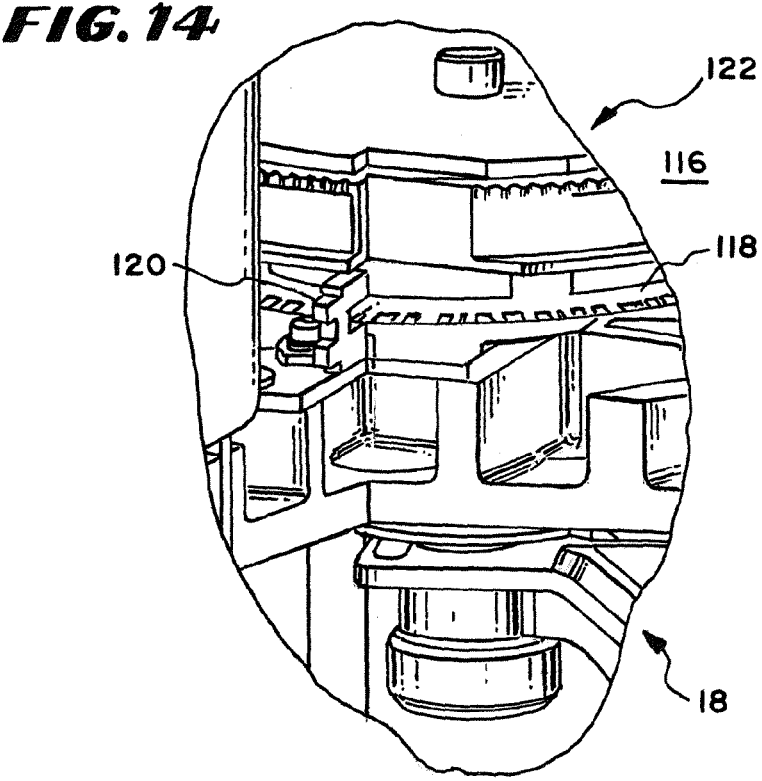

FIG. 14

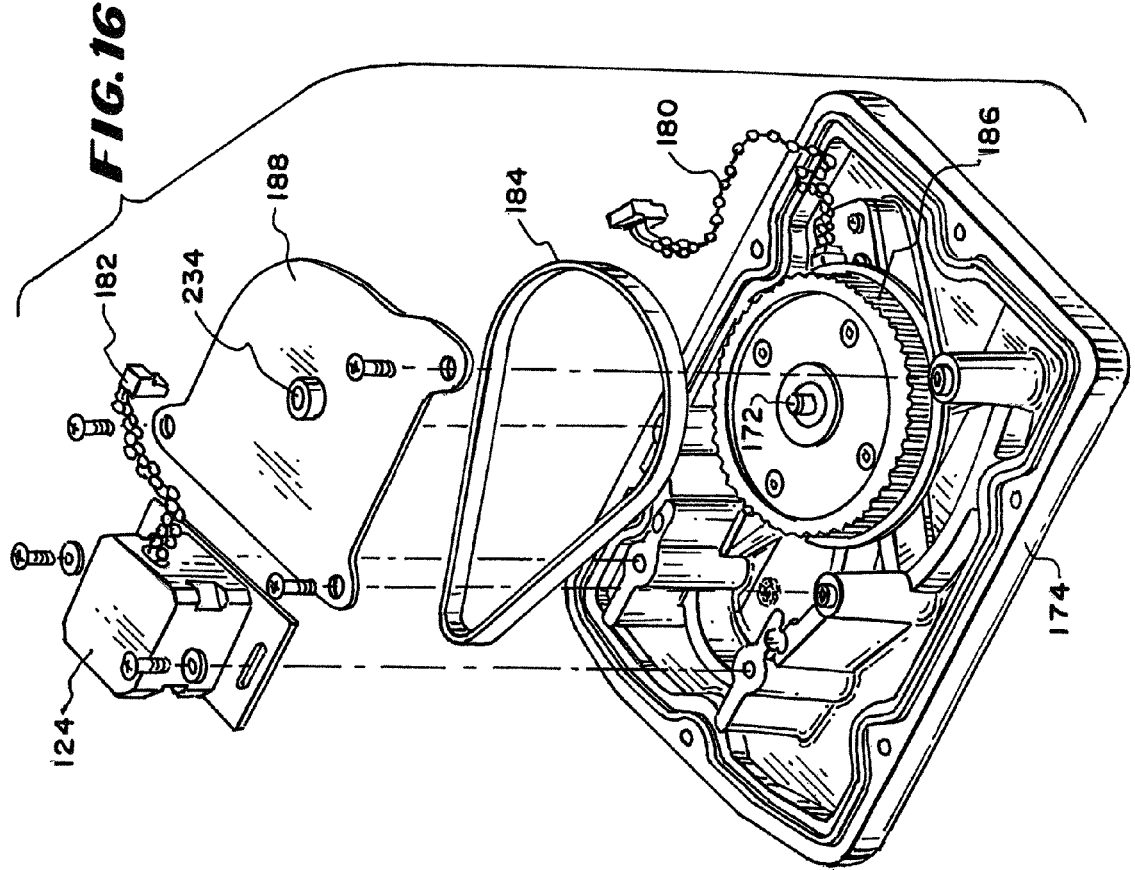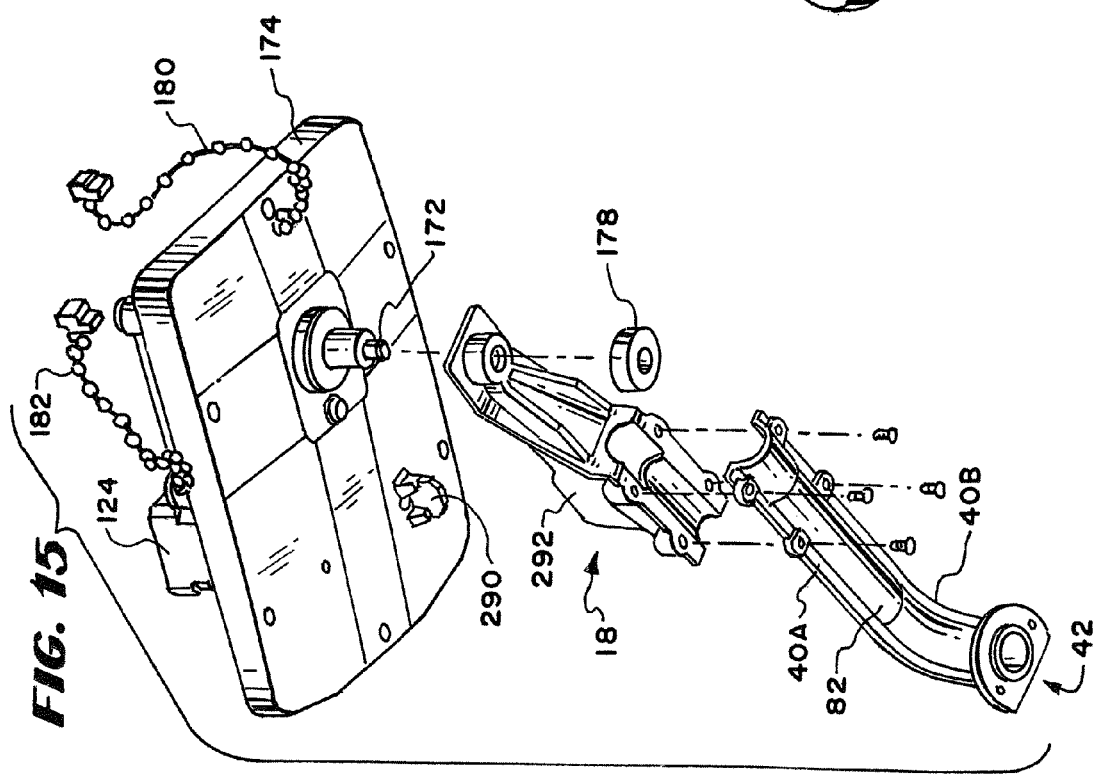

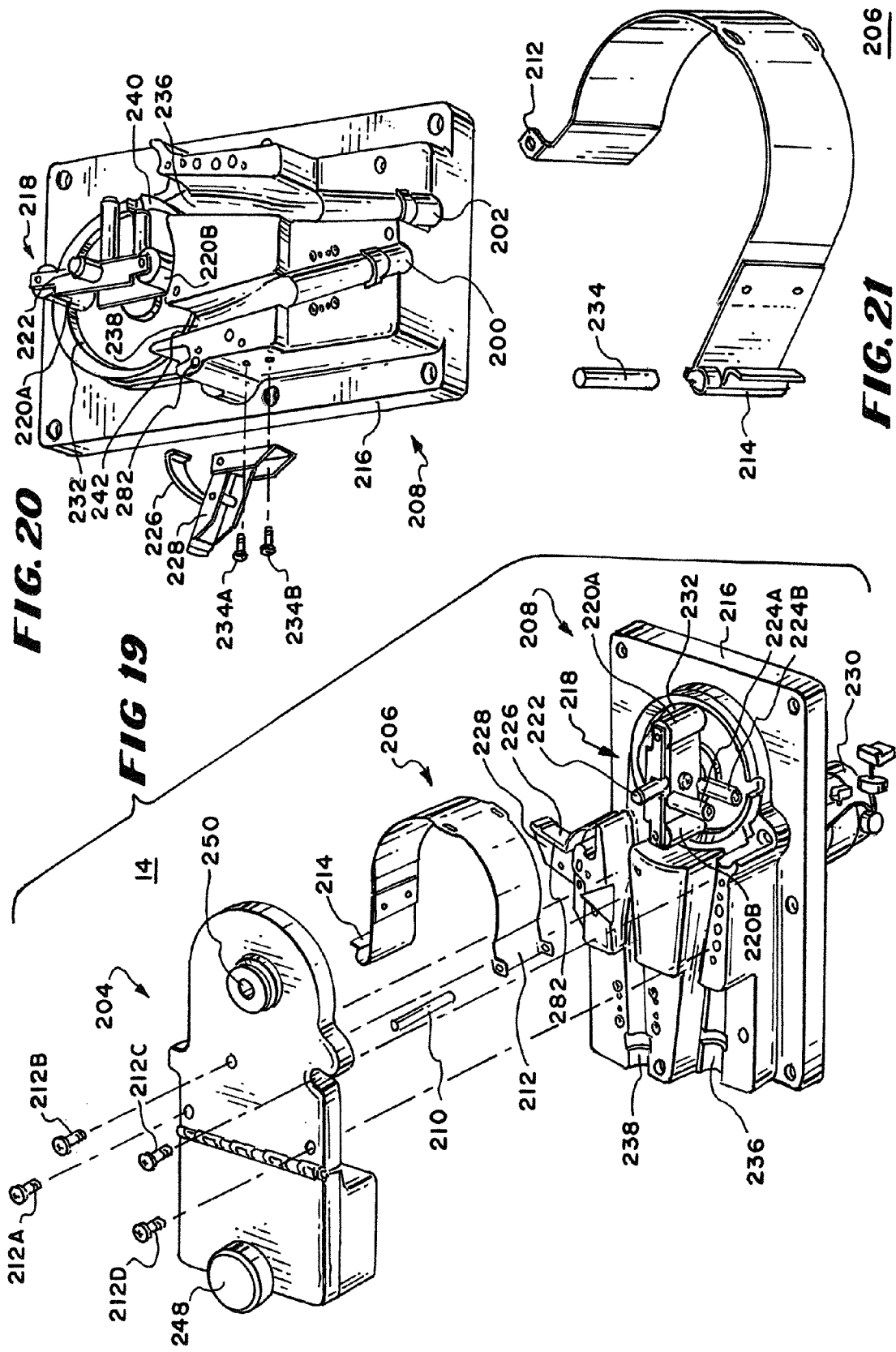

SAMPLE COLLECTOR AND COMPONENTS THEREOF

RELATED CASES

This application is a divisional application of U.S. parent application Ser. No. 11/980,261 filed Oct. 30, 2007, now pending, which is a divisional of U.S. parent application Ser. No. 11/430,606 filed May 9, 2006, now pending, entitled, SAMPLE COLLECTOR AND COMPONENTS THEREOF by inventors Robert R. Fielder, Frederick A. Nabity and Henry L. Walters.

BACKGROUND OF THE INVENTION

This invention relates to sample collectors and components thereof. Some of the components have independent utility and are described in connection with sample collectors and in connection with other types of equipment and methods.

It is known to apply a protective coat to equipment such as sample collectors to protect the equipment from harmful environmental effects such as corrosion. In the prior art, most equipment such as refrigerated sample collectors, refrigerators, freezers and air conditioners are constructed by adding one part at a time into an integrated design with some of the parts already coated or painted. The prior art method has a disadvantage in that it is difficult to adequately seal all of the joints of the system. Moreover, when the system requires repair, the system must be dismantled, reassembled and an attempt made to provide a corrosive resistant coating in all of the joints and other inaccessible places.

It is known to provide a separate heating element and controls for a system to warm up a compressor prior to running the compressor in cold weather. This approach has the disadvantage of being expensive and requiring additional electrical insulative protection.

Peristaltic pumps are known which include a connecting band that is opened to obtain access to the peristaltic tube. In the prior art, the pumping action tends to flex the restraining element and causes wear on the tube. Moreover, it is difficult to unlatch the prior art bands and to re-latch them. This problem is particularly aggravated with peristaltic pumps having less than three rollers. With less than three rollers, for easy removal of the tube, more than 120° must be readily openable for inserting the tubing. Peristaltic pumps include a guideways for the pump tube leading to the raceway. In the prior art the shape of the guideways causes the tube to be moved from side to side and at times to rub against edges of the raceway under the stress of the paddle rollers.

In the prior art, generally geneva mechanisms or other apparatus are used to move the distributor arm. In order to obtain precision positioning, the units always hold the arm at a location that is known. However, this prevents the arm from being freely rotated when the waste water sampler is not operating. Prior art systems attempting to provide an indexing system that identifies the location of the distributor use multiple circles of indicia in multiple channels to indicate numerical position and direction of movement. These systems have the disadvantage of being complicated and expensive.

SUMMARY OF THE INVENTION

Accordingly, it is an object of the invention to provide a novel refrigerated sampler.

It is a still further object of the invention to provide a novel low cost refrigeration system.

It is a still further object of the invention to provide a novel method for protecting a refrigeration system from a corrosive environment.

It is a still further object of the invention to provide a novel method of applying a protective coat.

It is a still further object of the invention to provide a novel method of forming a bottle rack.

It is a still further object of the invention to provide a novel bottle rack.

It is a still further object of the invention to provide a novel system for warming a compressor when the ambient temperature is low enough to hinder the starting of the compressor.

It is a still further object of the invention to provide a novel system for warming a compressor when the ambient temperature is low while using a minimum of parts.

It is a still further object of the invention to provide a novel system for warming a compressor that uses temperature sensors, a power supply, compressor motor windings as a heating element and thermostat system of the refrigeration system to implement its system.

It is a still further object of the invention to provide a novel totally integrated refrigeration system that is separate from cabinetry and can be easily removed.

It is a still further object of the invention to provide a novel peristaltic pump band.

It is a still further object of the invention to provide a novel peristaltic pump band latch that reduces flexing of the band.

It is a still further object of the invention to provide a novel peristaltic pump band that is easily latched and unlatched.

It is still further object of the invention to reduce the wear on peristaltic pump tubes.

It is a still further object of the invention to provide a peristaltic pump guideway that resists movement of the peristaltic pump tube from side to side in the raceway.

It is a still further object of the invention to provide a system for warming a compressor to ensure that it will not be pumping a liquid and thus be damaged.

In accordance with the above and further objects of the invention, the condenser and evaporator coils and orifice restrictor are mounted to a support unit and connected for operation. After these components are connected, a protective coat is applied to the combination and a coated condenser is mounted onto the same support unit to form a unitary frame that can be removed as a unit such as for servicing and can be reinstalled as a unit. The evaporator coils, condenser coils and a restrictor are coated after being connected, whereby an effective seal is provided for the restrictor, condenser coils and evaporator coils after they are assembled to the support. In the preferred embodiment, powder coating is used to penetrate into inaccessible locations. However, other coating materials and techniques can be used such as zinc based paints or epoxy materials. Moreover, instead of powder coating, the protective coat can be applied by dipping the connected compressor coils, evaporator coils, restrictor and supporting member in the protective material or by forming aerosols of the protective material or the like. Moreover, if aerosols not involving high temperatures are used or if the coat is applied by dipping, the compressor may be connected before the protective coat is applied.

The bottle rack for the sample collector is made by injection molding two halves of the rack each of which has a matching surface and a bottle positioning surface. The matching surfaces are fastened together by placing the matching surfaces together back to back whereby locating members are spaced apart a sufficient distance to provide stability to the bottles.

To position a distributor in the sample collector, an index disk rotates with the distributor. Each specific location is represented by one or more wide openings with smaller openings on each side of it. The smaller openings locate the unique code indicating the unique position. Each of the wider opening or openings define a code element. For example, two wide spaces next to each other between narrow spaces indicates a two character code. In the preferred embodiment, the number of stepping motor steps that occur during detection of a wide opening represents a code character and the two wide openings side by side represent two consecutive code characters. In the preferred embodiment, the code characters represent a number that is proportional to the steps of a stepping motor. While in the preferred embodiment, most locations are indicated by one or more wider openings with smaller openings on each side, other indicia, such as magnetic or opaque section, may be used in a similar manner. Moreover, any other sequence of indicia or different arrangement of openings that indicate a unique location may be used.

A peristaltic pump includes an openable metal pump band to hold the tube in place in a cylindrical rolled radius keeper. The metal pump band has a curved hook on one end that fits into the cylindrical rolled radius and rotates within it to reduce the flexing of the band as the pump rollers move the tube. The keeper mounted to the peristaltic pump is positioned to engage its hook, and hold it in place. A hook guide blocks the hook from passing above the cylindrical rolled radius. The peristaltic pump has contoured tube guides communicating with the raceway. The contoured tube guides are arranged to reduce movement of said peristaltic pump with the raceway as said roller paddle rotates.

To warm a compressor to a starting temperature during cold weather, the ambient temperature is measured and when the ambient temperature is lower than a preset temperature and the compressor is not running, current is applied to the motor windings to warm the compressor. The controls supply current to the coils at an amplitude too low to start the compressor motor or frequency different than that at which the compressor normally runs. The current is maintained low or at a frequency or a reverse voltage that does not alter the operation of the compressor. This provides heat to ensure there is no liquid in the compressor. The ambient temperature, the status of the compressor motor and the source of current are all determined using sensors and controls already on the refrigeration unit to operate the compressor, thus reducing the cost of the system.

From the above summary of the invention, it can be understood that the sample collector and the components that are used in the sample collector and other apparatus have several advantages, such as: (1) they provide an economical method of forming a bottle rack; (2) they provide a superior protective coat to equipment that may be used in a corrosive environment; (3) they provide an inexpensive position sensor that indicates a unique position with simple equipment; (4) they provide an improved peristaltic pump in which a metal band utilized to close the pump is more easily positioned; (5) they provides a superior peristaltic pump tube guideway that reduces the wear on the peristaltic tube; and (6) they provide a particularly inexpensive system for maintaining a compressor sufficiently warm in a cold environment for ease of starting.

BRIEF DESCRIPTION OF THE DRAWINGS

The above-noted and other features of the invention will be better understood from the following detailed description when considered in connection with the accompanying drawings, in which:

FIG. 5 is a block diagram of a method of making the refrigeration system of FIGS. 3 and 4;

FIG. 6 is a block diagram of a method of servicing the refrigeration system of FIGS. 3 and 4;

FIG. 8 is a simplified perspective view a portion of the embodiment of FIG. 7 illustrating an invention as it may be applied to wastewater samplers;

FIG. 9 is a simplified perspective view of a portion of the embodiment of FIG. 8;

FIG. 10 is a simplified perspective view of another portion of the embodiment of FIG. 8;

FIG. 11 is a simplified perspective view showing a stage in the development of an embodiment of FIG. 8 that comprises the embodiments of FIGS. 9 and 10;

FIG. 12 is a simplified perspective view of the embodiment of FIG. 11 in a further stage of fabrication;

FIG. 13 is a flow diagram of a process of making a bottle rack;

FIG. 14 is a fragmentary perspective view of a portion of the embodiment of FIG. 7;

FIG. 15 is a perspective view of another portion of the embodiment of FIG. 7;

FIG. 16 is a simplified exploded perspective view of a portion of the embodiment of FIG. 14;

FIG. 19 is an exploded simplified perspective view of an embodiment of an invention as it may be used in a pump;

FIG. 20 is a simplified perspective view of the embodiment of FIG. 19;

FIG. 21 is a simplified perspective, partly exploded away of a component of the embodiment of FIG. 19;

DETAILED DESCRIPTION

Figure 1:
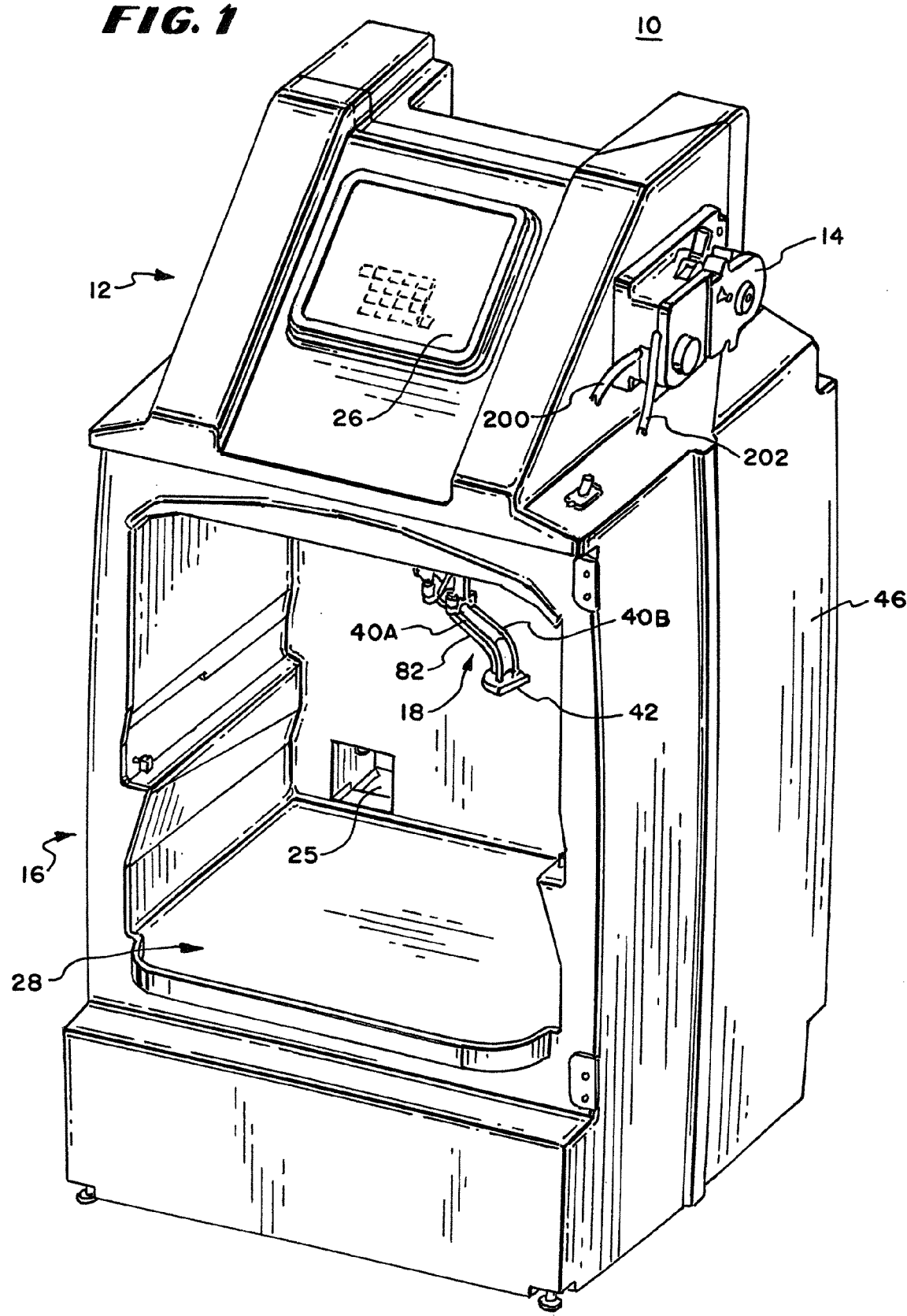
FIG. 1 is a simplified, fragmentary, partly-exploded view of a sample collector which incorporates embodiments of the invention.

In FIG. 1, there is shown a simplified perspective view of a sample collector 10 which is one type of apparatus that may include inventions described hereinafter and which has as its principal component parts a control system 12, a peristaltic pump 14, and an enclosed refrigerated sample bottle compartment 16. The enclosed refrigeration system and sample bottle unit 16 is housed in an enclosure and has separately mounted above it the control system 12 to control the collection of samples in the refrigeration system and sample bottle unit 16 and a peristaltic pump 14 which, under the control of the control system 12, may pump liquid samples such as waste water samples into bottles included within the refrigeration system and sample bottle unit 16 (the bottle rack and bottles are not shown in this view for clarity).

The control system 12 includes a touch screen 26 for the control system 12. The peristaltic pump 14 is mounted to the side of the control system 12 and is controlled thereby to draw samples and cause them to flow into bottles within a refrigerated compartment 28. For this purpose, the peristaltic pump 14 includes pump inlet and outlet tubing 200 and 202. The enclosed refrigeration system and sample bottle unit 16 includes a refrigerated sample bottle compartment 28 and a refrigeration system 46. The refrigeration system 46 cools the refrigerated compartment 28 which is designed to include sample bottles and a distributor arm which fills the bottles with samples in accordance with the control system 12. The peristaltic pump 14 under the control of the control system 12 determines when to draw a sample and the amount of sample to be deposited in the bottles. The control system 12, refrigeration system and sample bottle unit 16 and peristaltic pump 14 cooperate together in the manner described in U.S. Pat. No. 5,915,932, the disclosure which is incorporated herein by reference.

The refrigerated sample compartment 28 includes a distributor arm 18, an opening for electrical connections a vent opening 25 through which air leaves the compartment 28. A port and fan shown at 38 (FIG. 2) blows cooled air into the refrigerated compartment 28. The distributor arm 18 includes a distributor outlet 42 through which samples flow into sample bottles, a distributor hose 82 and side support members 40A and 40B for the distributor hose 82. The peristaltic pump 14 is positioned with its paddle rollers having an axis of rotation that is horizontal so that it opens to the side. However, it may be positioned and hinged to open in other directions or orientations.

Figure 2:
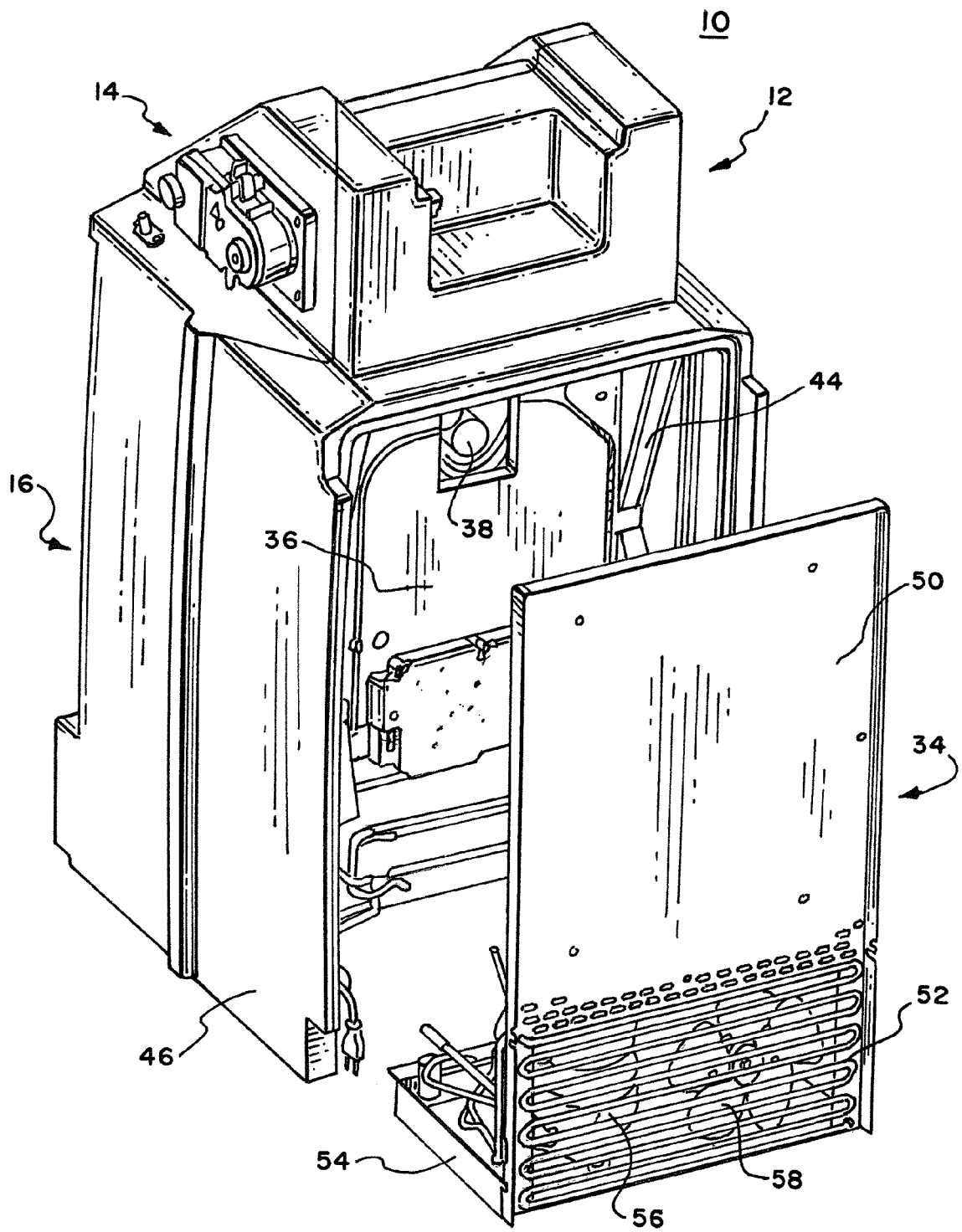
FIG. 2 is another view of the sample collector of FIG. 1 illustrating an embodiment of the invention as it would be applicable to the sample collectors.

In FIG. 2, there is shown another simplified perspective view of a sample collector 10 from another side having the control system 12, the peristaltic pump 14, the enclosed refrigeration system and sample bottle unit 16, the refrigeration section 46, with the cooling assembly 34 shown removed. A cool air compartment 36 within the refrigeration section 46 includes a cool air space port 38 and a computer-compressor electrical connector 44. Cool air flows through the port 38 into the refrigerated bottle compartment 28 (FIG. 1). The cooling assembly 34 includes a back plate 50, condenser coils 52, a bottom support panel 54, a compressor unit 56 and a fan 58. The compressor unit 56, the fan 58, the back plate 50 and the condenser coils 52 are mounted to the plate. Also the evaporator coils (not shown in FIG. 2) are mounted to the back plate 50 so as to be supported on the bottom support panel 54. With this arrangement, the compressor 56, the fan 58, condenser 52 and evaporator coils are all moved as a single unit into the cooling compartment 36 or removed from the cooling compartment 36. This permits easy removal for service and the application of a protective coating such as by powder coating processes substantially coating the entire cooling system 34 as a unit.

The sampling system 10, in one application is utilized to sample wastewater in a corrosive environment. By separately assembling multiple units together, a protective coating may be applied after these units are connected which permits a better seal than when the individual units are covered with a protective coating and then interconnected to each other since the connecting points are inadequately protected if they are coated first and then connected. Moreover, by using a powder coating technique that causes the powder to flow into narrow spaces when the unit is already connected, unprotected connecting points are reduced and failure because of corrosion is reduced.

In some embodiments, it is not possible to connect all units together. For example, the compressor is not connected prior to applying a protective coat to other units because the temperature at which powder coating is applied may damage the compressor. However, the other units are coated and then the compressor is connected leaving only the compressor connections to be separately coated. Thus the condenser coils 52, evaporator coils, the fan unit 58, the restrictor, any other components and the connections between them may be coated after they are assembled and then special care taken for the few remaining connections to provide superior protection. Other coating materials and techniques such as zinc based paints applied as an aerosol or in which the connected units are dipped may permit the compressor to be connected before the combination is coated.

Figure 3:
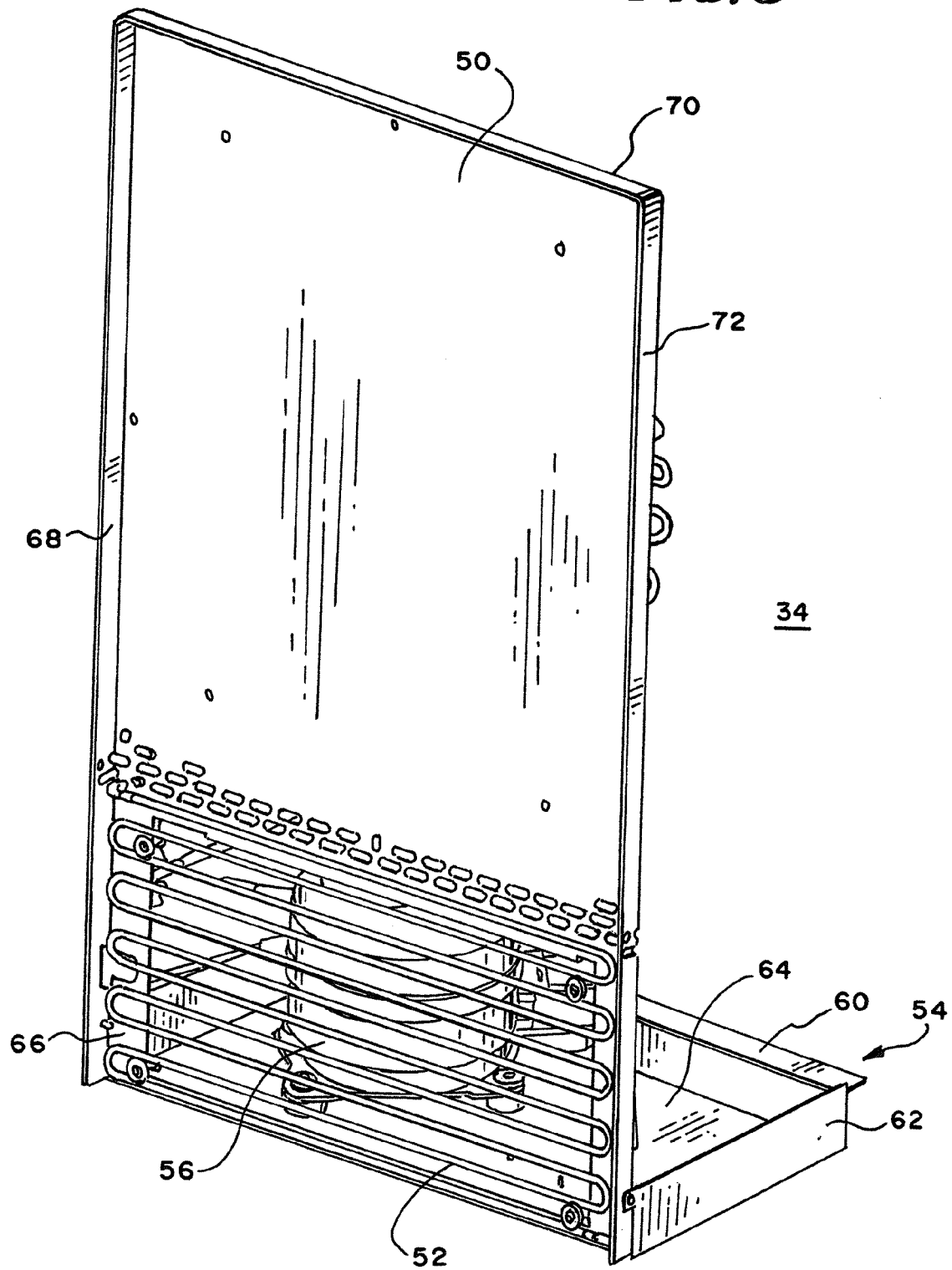
FIG. 3 is a perspective view of a refrigeration unit incorporating an embodiment of the invention as applied to a sample collector.

In FIG. 3 there is shown a perspective view of the cooling assembly 34 showing in greater detail the bottom support 54 having side members 62 and 66, a bottom member 64 and an inner wall 60. The bottom wall 64 supports the compressor 56 and a cooling fan (not shown in FIG. 3) with the back plate 50 having side walls 68 and 72, a top wall 70 and the exposed condenser coils 52. the condenser coils are positioned so that a fan 58 (FIG. 2) flows air outwardly to remove heat.

Figure 4:
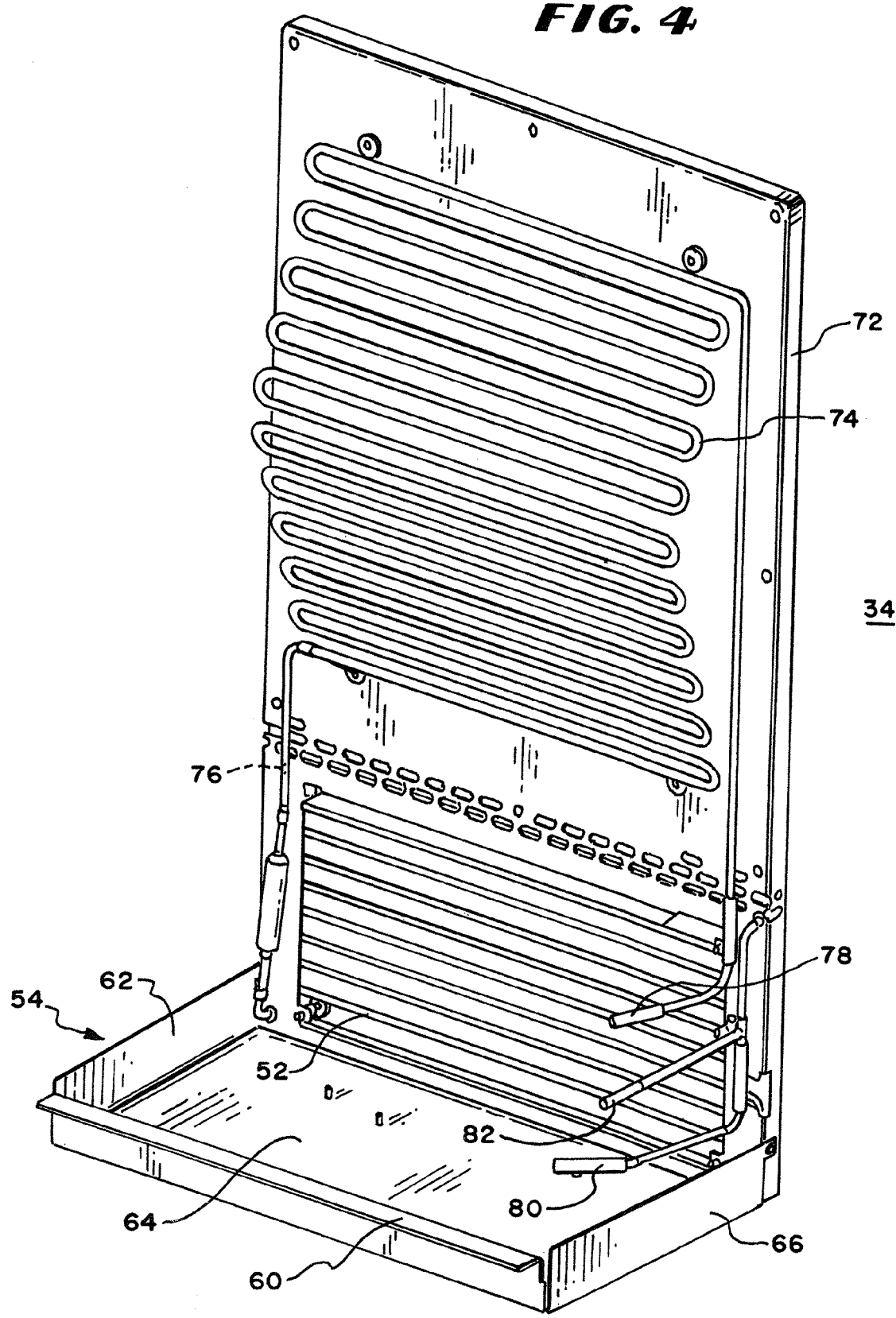
FIG. 4 is a fragmentary perspective view of the refrigeration system of FIG. 3 taken from another angle.

In FIG. 4, there is shown a perspective view of the cooling assembly 34 from the opposite side as shown in FIG. 3 with the evaporating coils 74 shown mounted to the plate 72 to cool the cool air compartment 36 (FIG. 2). As shown in this view, a precision orifice 76 within the tubing provides an appropriate restriction to permit the building up of pressure in the condenser coils 52 and expansion in the evaporation coils 74. Connections to the evaporator coils 74 and the compressor 56 (FIG. 3), the condenser coils 52 are shown at 78, 80 and 82. These connections are made after powder coating or otherwise insulating the coils and restrictor and separately insulating the compressor. However, they are easily accessible by removing the entire cooling assembly 34 and good seals may be obtained to avoid exposed locations that will corrode in the corrosive environments in which sample collectors are sometimes used. While an orifice restrictor 76 is used as the restrictor in the preferred embodiment, a capillary restrictor could be used instead. However, the small size and long length of a capillary restrictor make it prone to chipping the protective coat, thus reducing its protective ability. Because an orifice restrictor is small, short and confined within the transfer tubing, the unit including it is more rugged and durable in the anticipated environment than units using a capillary restrictor.

In FIG. 5, there is shown a flow diagram 90 including the step 92 of assembling condenser coils, evaporation coils and a fan on a single unitary frame, the step 94 of powder coating the assembly of step 92, the step 96 of mounting the compressor on the unitary frame and connecting the compressor to the condenser and evaporation coils, the step 98 of sealing the connections between the compressor and evaporation coils and the step 100 of mounting the unitary frame to the main refrigerated sampler. With this process, a protective coating may be efficiently applied and provide better protection then coating individual units and mounting them to the refrigerated sampler in a step by step process as the sampler is built up to include the necessary components. Moreover, the unitary frame also permits more economical servicing of the units since it can be easily disconnected and moved from the refrigerated sampler to perform service on it. In this specification, the words "unitary frame" means the combination of support members and multiple components that include at least condenser and evaporator coils of a refrigeration unit that are supported together and may be removed as a unit from a refrigeration system and returned to the refrigeration unit to be connected as a single unit.

In FIG. 6, there is shown a flow diagram 102 including the step 104 of unfastening the unitary frame from the refrigerated sampler, the step 106 of pulling out the unitary frame, the step 108 of servicing the refrigerated sampler and principally the components mounted on the unitary frame and the step 110 of pushing the unitary frame back within the refrigerated sampler and fastening it in place. With this arrangement, the refrigerated sampler may be more conveniently serviced by either removing the unitary frame to a location for servicing or merely removing it easily from the refrigerated sampler for servicing and even by replacing it with a different unitary frame temporarily while service is performed on the prior unitary frame. Access is more easily obtained to repair the parts and provide a protective coating where the coating may have been removed or damaged.

In this specification, the word "restrictor" shall include both capillary and orifice restrictors designed to provide a pressure differential between the evaporator coils and the condenser coils of a cooling unit. The words "final closure" shall mean an outside member that provides a suitable wall for the refrigerated sampler with the proper appearance and protection and yet is easily fastened to the refrigerated sampler. It permits easily fastening and unfastening without other obstructions so that it may be quickly unfastened to pull the unitary frame out and quickly fastened to provide a finished appearance to the refrigerated sampler. In this specification, the words "special protective coat" shall mean a coat specially adapted to protect surfaces of components and connections between components in a corrosive environment. In the preferred environment, this coat should be obtained by the process known as powder coating after at least two of the components have been connected together so as to permit effective protection to the connections themselves in a corrosive environment. In the preferred embodiment, all of the components on the unitary frame except for the compressor are connected before the special coat is applied.

Figure 7:
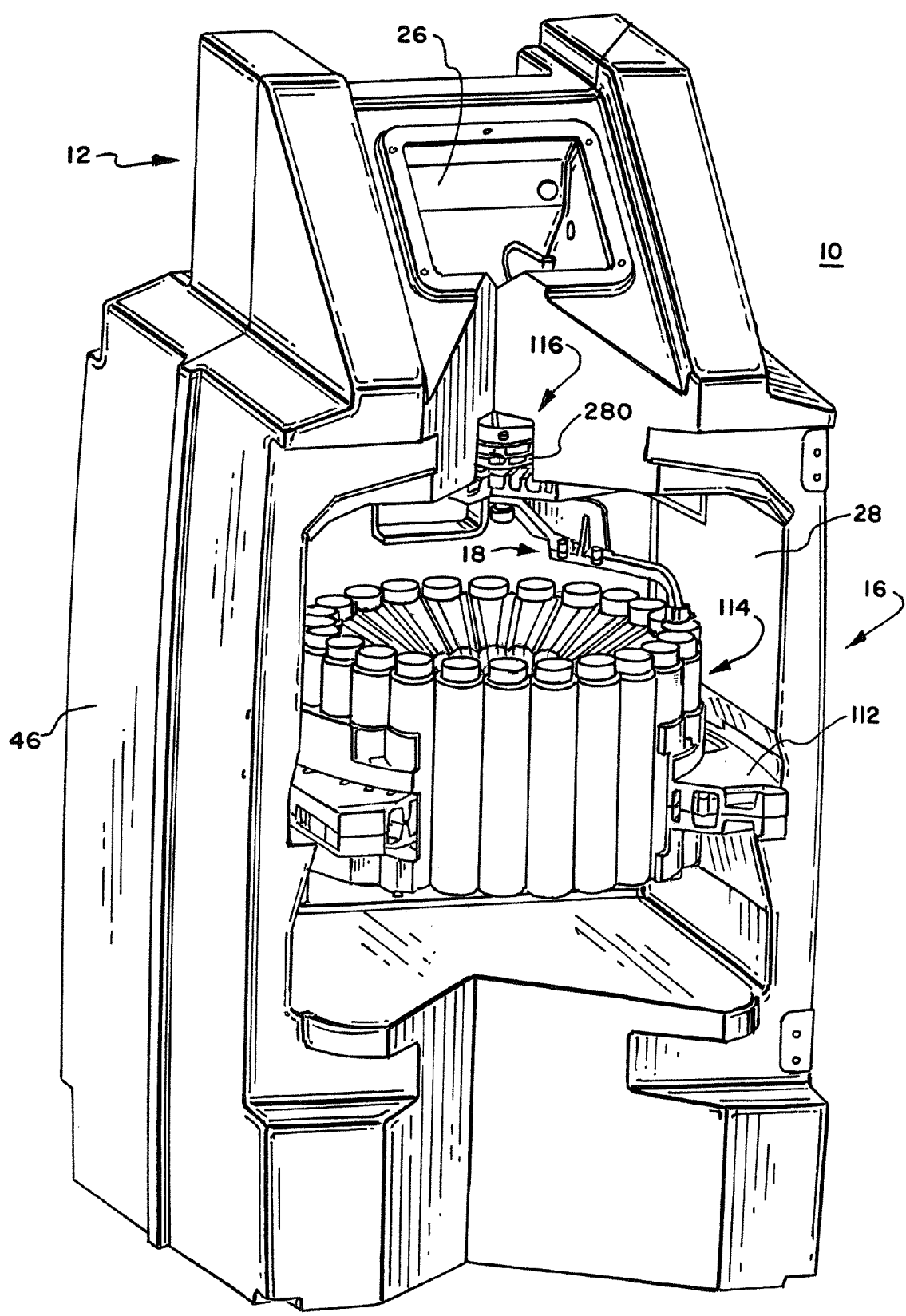
FIG. 7 is a partly-broken away perspective view of the sample collector of FIGS. 1 and 2 illustrating an embodiment of the invention as applied to the sample collectors.

In FIG. 7, there is shown another perspective view of the refrigerated sampler 10 broken away to show the refrigerated sample compartment 28 with a plurality of sample bottles 114 mounted in a bottle rack 112 within the refrigeration compartment 28. A distributor arm 18 is shown positioned over a bottle. During sampling a distributor arm positioning assembly 116 determines the position of the distributor arm 18 even though the distributor arm 18 may be freely moved by hand and thus have been moved out of position. Thus, accidental moving of the distributor arm 18 such as to remove or insert a bottle rack still permits operation because the distributor arm positioning assembly 116 detects the location of the distributor arm 18 and moves the distributor arm 18 to the starting position by a stepping motor or any other drive means such as for example, an indication motor, a synchronous motor, a solenoid or linear actuator. The bottle rack 112 is mounted to a ledge within the refrigeration compartment 28 on which it rests so that it can be easily removed along with the sample bottles and a new rack with new sample bottles can be placed inside the refrigeration compartment 28. A fan 280 blows cold air into the refrigeration compartment 28.

In FIG. 8, there is shown a simplified perspective view of the distributing arm positioning assembly 116, the distributor arm 18, and the bottle rack 112. The bottle rack 112 includes two injection molded sections 112A and 112B molded from a single cavity and positioned with their respective bases 126A and 126B in contact with each other. Each of the bases 126A and 126B has a cylindrical supporting and positioning wall 128A (FIG. 9) and 128B (FIG. 10) extending from it. Each of these walls has a surface which contacts a corresponding one of the sample bottles 114 to provide a contact point against the bottle. Thus the two units with the bottoms of their bases 126A and 126B in contact with each other provide two points of contacts against the surfaces of each bottle so as to firmly position them on one side. A central cylindrical member positions them on their inner surface (not shown in FIG. 8). The distributor arm 18 is located so as to have a central axis of rotation at the center of the circle of sample bottles within the bottle rack 112. Its outlet is thus positioned in sequence over the bottles by a stepping motor.

Figure 18:
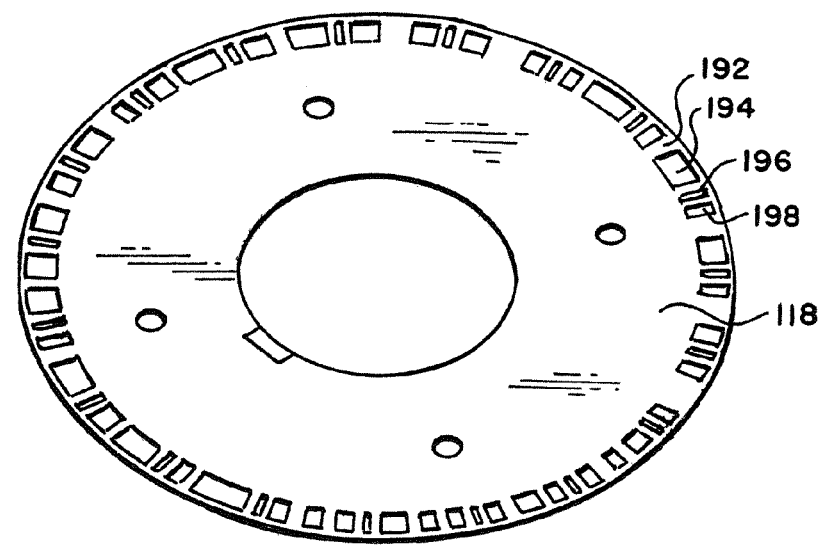
FIG. 18 is a perspective view of an index disk that is component of the embodiment of FIG. 14.

The distributor arm positioning assembly 116 includes a stepping motor 124, a distributor assembly 122, an index position sensor 120, and an index disk 118 (FIGS. 14 and 18). The index disk 118 has encoded on its periphery a code for each position. It rotates together with the distributor arm 18 so that the sensor 120 detects the position of the index disk 118 and thus the corresponding position of the distributor arm 18. The difference between the sensed position and the position that the distributor arm 18 is determined by a microcontroller which controls the stepping motor to move the distributor arm 18 to the proper position.

In FIG. 9 there is shown a simplified perspective view of a bottle rack half 112A having its base 126A, the cylindrical supporting and positioning wall 128A, handles 138A, 240A, 242A and 144A and bottle positioning members 130A, 132A, 134A and 136A. The positioning devices such as 134A have a central arc for receiving the surface of one sample bottle and two arced side members each of which contacts another sample bottle. The three sample bottles positioned by each of the positioning members controls the position of all of the sample bottles between two positioning members. With this arrangement, the location of the bottles may be calibrated to correspond to the code on the index disk 118. The code on the index disk for the first bottle is set to correspond to the numeral one on the base 126A as shown at 242 with the locations of the remainder of the bottles being indicated on the top surface of the base 126A.

In FIG. 10, there is shown a perspective view of the second rack half 112B of the bottle rack 112 having positioning members 130B, 132B, 134B and 136B (134B and 136B not being visible in FIG. 10). These are shaped in the same manner as the corresponding bottle positioning members in the first rack half 112A (FIG. 9). Similarly, since the base 126B is molded in the same cavity as the base 126A (FIG. 9) and the cylindrical supporting and positioning wall 128B is formed in the same cavity as 128A, the two halves are identical as they are molded. However, as shown in FIG. 10, both halves are molded with eight ribs extending radially from a connecting point to the bottle cylindrical supporting and positioning wall 154A-154H. However, in the first rack half 112A, the ribs are trimmed off before the bases and positioned together. Spring members 152 are shown in position to snap into openings in the refrigerated compartment 28 to latch the rack in place. Each of the two bases has positioning members 130B to 136B (FIG. 11) which are located together for exact positioning.

With this arrangement, the bottle rack may be economically molded using a single cavity injection mold and provide stable positioning of the bottles. With the two bases positioned together, the distance between the positioning devices on the base 112A with the corresponding positioning member on the base 112B is a stability design distance. In this specification, the words "stability design distance" or similar words means the distance between two positioning surfaces on a stabilizing member that is sufficient to hold an item without wobbling about at least one point. A single stabilizing member may include multiple stability design distances one for each possible pivot point. Multiple stabilizing members may be used to stabilize one item and a single stabilizing member may stabilize more than one item. A positioning surface is a surface that is in contact with the surface of the item to be stabilized to hold it in position. In the preferred embodiment, the surface is the outer lateral surface of a sample bottle with the positioning members holding the sample bottle in position.

In FIG. 11, there is shown a bottle rack 112 in the process of assembly with the two rack halves 112A and 112B being positioned against each other to be fastened in place with the screws 158A-158H that are threaded into corresponding holes. As shown in this view, the ribs 154A-154H are left at the bottom of the rack so that the bottles have their bottom against the ribs and their open tops extending upwardly. With each of the bottles being supported by two of the positioning members 130A-136A (not shown in FIG. 11) and 130B-136B. Thus the two positioning members such as for example 130A and 130B contact a bottle in two locations which are stability design distance apart.

In FIG. 12, there is shown a rack with the rack halves 112A and 112B positioned together to form a rack with a bottom surface 262. The bottles rest on the bottom surface 262 mounted underneath the ribs 154A-154G (FIG. 11). The center of the bottom surface 262 includes a circle of air flow control openings 142. The two aligned positioning members such as for example 134A and 134B (not shown in FIG. 12) position a bottle against side to side wobbling such as for example wobbling can be tangential to the cylinder 128A and 128B radial to the cylinder formed by the walls 128A and 128B. Because the bottles touch each other between the positioning members 130A, 130B-136A, 136B (not shown in FIG. 12), they are prevented from movement between the position members by the adjacent bottles as long as the adjacent bottles have relatively straight sides. Thus the positioning members align the bottles straight up and down in the tangential direction and prevent them from wobbling and the cylindrical walls prevent them from tilting in a radial direction or wobbling in the radial direction or moving out of position.

In FIG. 13, there is shown a flow diagram 164 of a step in manufacturing a bottle rack comprising the step 166 of preparing a single cavity mold for injection molding one rack half with at least one positioning surface for each bottle to be positioned, which positioning surface is one half of a stability design distance from one end of a half rack, the step 168 of injection molding two half racks for each rack desired, and the step 170 of inverting one half rack and fastening it to another half rack with one side of each half rack in contact so that at least one stabilizing member is formed with the one end being centered between two positioning surfaces. With this approach, a single cavity injection mold may be used to manufacture all of the principal parts of the bottle rack.

Figure 17:
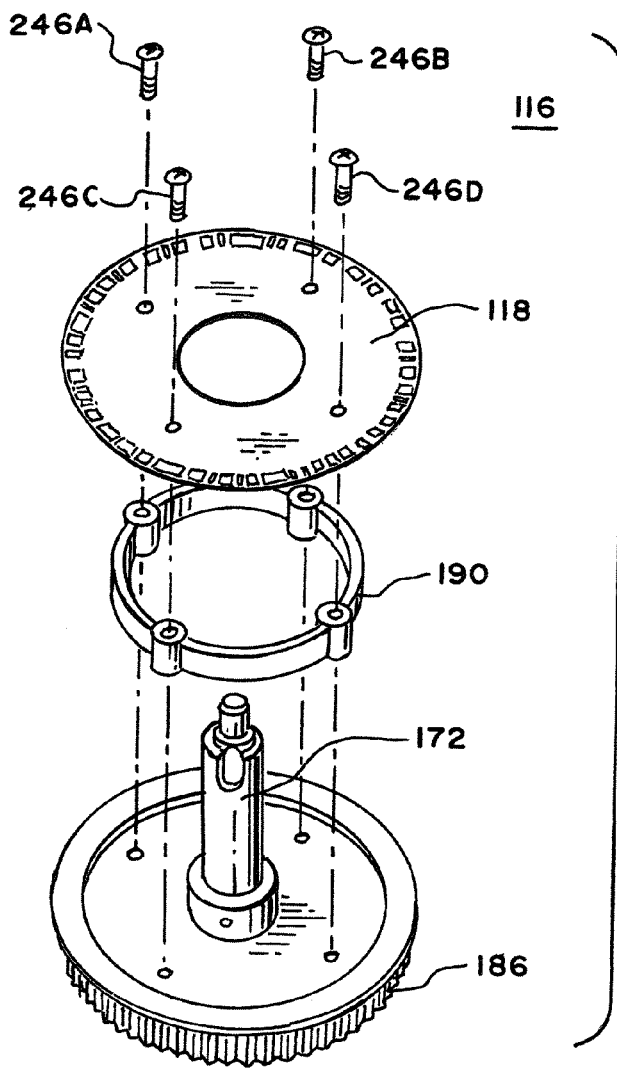
FIG. 17 is an exploded perspective view of another portion of the embodiment of FIG. 14.

In FIG. 14 there is shown a fragmentary view of a portion of the distributor arm positioning assembly 116 having a distributor assembly 122, an index disk 118, a sensor 120 and a portion of the distributor arm 18. As best shown in FIG. 17, the index disk 118 is fastened by screws to rotate with the distributor arm 18 and is aligned so that a code on its surface indicating the position of the distributor arm passes under the sensor 120. The code on the disk 118 consists of spaced-apart openings in the disk of different widths and combinations although any code could be used including magnetic codes or translucent portions or the like. In the case of a magnetic code, a magnetic pick up would be utilized. In the preferred embodiment the openings are made in a metal disk economically. Preferably, they are made lithographically and spaced to indicate a multiple of steps of the stepping motor. The sensor 120 includes a light source, which in the preferred embodiment is an LED, and a photocell, embedded in the sensor so that the index disk 118 passes between the sensor 120 with its code being directly between the photoelectric pick up and the LED. In this manner, signals are supplied from the sensor 120 and signals from the sensor 120 are supplied to a control system 252 (FIG. 22) indicating the exact position of the distributor arm 18.

In FIG. 15, there is shown a simplified, partly broken away perspective view of the distributor arm 18 having a stepping motor 124 connected through a conductor 182 to a source of power, a conductor 180 connected to the sensor 120 (FIG. 14) and to a control system 252 (FIG. 22) to indicate the position of the index disk 118 (FIG. 14) and distributor arm 18 and a drive shaft 172 driven by the distributor in synchronism with the index disk 118 (FIG. 14). The distributor arm 18 includes a hose 82 having an opening 42 at one end and supporting members 40A and 40B to support it as it moves in a circle about the drive shaft 172 with its outlet 42 being offset from the longitudinal axis of the shaft 172 a sufficient distance so that with the shaft 172 being positioned at the center of the ring of sample bottles 114 (FIG. 8), the opening will pass over the openings in the bottles. A nut 178 holds the distributor arm 18 to the shaft 172.

In FIG. 16, there is shown an exploded simplified perspective view of the distributor arm positioning assembly having the stepper motor 124, a shaft plate 188, a drive belt 184, a distributor gear 186 and the distributor base 174. The stepping motor drive belt 184 engages the gear 186 in one portion and the stepping motor output shaft which passes through a center bushing 234 of the shaft plate 188 to drive the gear 186 below the shaft plate 188. With this arrangement, as the stepping motor 124 steps from position to position it moves the drive belt 184 in synchronism which in turn turns the gear 186 to turn the distributor arm 18 and the index disk 118 (FIG. 14). Power is applied to the motor 124 through the conductor 182 and signals are received from the sensor 120 (FIG. 14) through the conductor 180.

In FIG. 17, there is shown a exploded view of a portion of the distributor arm assembly 116 showing the index disk 118 spaced from the distributor gear 186 by a spacer 190 and positioned with respect to the distributor output shaft 172, the distributor gear 186, and the index disk 118 by screws 246A-246D which pass through or into each of them to maintain them in synchronism.

In FIG. 18, there is shown a perspective view of the index disk 118 having openings to receive the screws 246A-246-D (FIG. 17) and a code placed on the periphery formed of opaque portions one of which is labeled 192 and openings of different sizes shown at 194, 196 and 198. These openings provide a unique code which indicates the exact location of the disk and thus the location of the outlet of the distributor arm with respect to the sample bottles. In the preferred embodiment, the unique code is based on the number of steps of a stepping motor as described above.

Generally, the index disk includes a sequential series of codes, each indicating a position on the disk. While in the preferred embodiment, the codes indicate a unique position on a disk, they can indicate a unique position on any object which moves with respect to a sensor that senses the codes. Each unique code at a unique position is identified by a code identification character and a code character or other unique criteria such as for example, a pattern of indicia that does not repeat. The pattern may by comprised completely of code characters or may be separate from the code characters. It can be spacial or numerical and consist of any indicia including light and dark areas. Each code character is indicated by at least one code identification character to separate it from other code characters. In the preferred embodiment, two code identification characters are used, one on each side of the code character.

As shown in FIG. 18, opaque spaced portions separate openings. Narrow openings are code identification characters that indicate the presence of code characters identifying the location. For example, in FIG. 18, the narrow slots such as 196 indicate the presence of a code between it and the next narrow slot. Between two narrow slots, there are wider portions such as 194 and 198 that constitute code characters. A code may include a plurality of code characters. In the preferred embodiment, the narrow portions have a width of seven to thirteen distances of a stepping motor step. The number of steps it take to cross the distance of the wider openings represents a code character. In the preferred embodiment, this is considered a numerical value. Where there are multiple adjacent wide spaces not separated with a narrow space, each of the wide spaces indicates a different code character which together form a code.

In the preferred embodiment, when the distributor arm is not being moved by the stepping motor, the stepping motor is de-energized and the arm can rotate freely. However, once a command is given to move a distributor over a bottle, the stepping motor moves the distributor arm in a direction as commanded by the microcontroller. The microcontroller controls each step by issuing a signal for that step. It remembers the direction that the distributor arm was last moving and moves the distributor arm in that same direction as a start. However, as soon as the distributor arm recognizes a code portion from a narrow opening, it determines if it is moving in the desired direction to reach the bottle in a short time. If not, the microcontroller has the stepping motor change directions. The one or more code characters are recognized in the microcontroller as being the same specific location whether they read in one direction or in the opposite direction.

A stop is provided at 290 which engages the distributor at 292 (FIG. 15) in the event of a malfunction in which the code is misread and the microcontroller attempts to move too far in one direction. When that happens, the microcontroller recognizes that the stepping motor has attempted to move too large a distance and does not order a sampling operation. Because this system recognizes unique locations, in many instances, the microcontroller continues operating in accordance with the procedures as described in the aforementioned patent.

In FIG. 19, there is shown an exploded perspective view of a peristaltic pump 14 having a peristaltic pump cover 204, a metal pump band 206 and a pump base 208. The pump base 208 has mounted to it a roller paddle 218 driven by a motor 230 with two rollers 220A and 220B mounted on the ends of the paddle to roll along a raceway 232. Two positioning posts 224A and 224B hold a peristaltic pump tube 200 (not shown in FIG. 19) in position in the raceway 232 while the roller paddle 218 rolls against it driven by the motor 230 and an output shaft 222 to pump liquid through the peristaltic pump tube.

Two peristaltic pump grooves 236 and 238 hold the peristaltic pump tube in a loop with a portion of it along the raceway 232 with one end of it extending along the contoured tube guide 238 and the other end along the contoured tube guide 236. The contoured tube guides 236 and 238 are spaced from each other and the contoured tube guide 236 starts at an elevation lower than the raceway 232 and increases in height up to the raceway 232 while the contoured tube guide 238 is at an elevation higher than the raceway 232 and gradually lowers to an elevation at the raceway 232. The contoured tube guides 236 and 238 are shaped so that they apply the same bias to the peristaltic pump tube to maintain it in the raceway against the movement of the rollers 220A and 220B to avoid it from being moved from one side to another and being pinched.

In this specification, the words "contoured tube guide" means a tube guide leading to or from a raceway with a shape designed to reduce the tendency of the tube to move from the center of the raceway during a pumping operation. The contoured tube guide on one side of the raceway starts with a bottom edge below the top edge of the raceway and other starts with its bottom edge above the top edge of the raceway. Both of them connect with the raceway with their bottom edge equal to the top edge of the raceway. The curvature leading to these points is shaped, partly by trial and error, to provide a bias to the tube that reduces its motion from side to side to a minimum and thus avoids excess cutting and wear of the tube which otherwise would occur as the rollers force it against edges or the like of the raceway.

The edges of the raceway are curved to reduce the tendency to cut the peristaltic tube. The raceway 232 has rounded edges to further avoid the wear on the peristaltic pump tube as the rollers exert a force in the direction of the flow of the liquid. The curves of the contoured path place a bend in the peristaltic pump tube in opposite directions with one rising and the other lowering in a symmetrical manner and slanting slightly toward the center of the raceway. With this contour, bias is placed on the peristaltic pump tube to resist its moving from one side to the other and thus the peristaltic pump tube avoids wear and lasts longer.

The metal pump band 206 receives a hinge pin 210 on one end permitting it to open approximately 180 degrees so as to provide access to the peristaltic pump tube when opened but to protect it and hold it in place when closed. A hook 214 on one end fits within a cylindrical rolled radius 226, which has a radium of curvature similar to the radium of curvature of the hook 214 so as to permit rolling motion between the two. This rolling motion reduces the flexing of the band. engages a keeper 226 to hold it in place when it is not opened. A toggle latch pulls the hook 214 to stretch and hold the band. A guide 282 prevents the hook 214 from being positioned too high and over the cylindrical rolled radius. The peristaltic pump cover 204 includes a hinged portion, a thumb screw 248 and an axle seat 250. The axle seat 250 is aligned with the output shaft 222 and when the cover 204 is in place provides a seat to stabilize the output shaft 222 for the roller paddle 218. The thumb screw 248 holds the cover 204 at one point to the base 216 and screws 212A-212D hold the cover 204 to the base 216 at other locations.

In FIG. 20, there is shown another perspective view of a base 208 showing two ends of the peristaltic pump 200 and 202 within the contoured tube guides 236 and 238 but broken away so that it is not shown entering the raceway 232. On one end of the base, there is mounted by screws 234A and 234B a keeper and keeper guide 228 positioned so that the hook 214 (FIG. 19) on the end of the metal band 206 (FIG. 19) engages the keeper is held within the cylindrical rolled radius. The guide 282 prevents the hook from being positioned above the cylindrical rolled radium 226 rather than within it. Because the axis of rotation of the roller is horizontal and there are only two rollers the sides of the pump cover must provide at lest 180 degrees when operating. However, for easy installation or replacement of a tube when the band is opened, access shall be provided for at least 90 degrees and preferably between 120 degrees and 180 degrees in the preferred embodiment.

In FIG. 21, there is shown a perspective view of the band 206 showing the hinge 212 which engages the hinge pin 210 (FIG. 19) to prevent opening and closing of the band 206. On the end 214 there is mounted a magnet 234 which cooperates with a reed switch (not shown in FIG. 21) to detect when the band is open or closed in a manner described more fully in the aforementioned U.S. Pat. No. 6,354,345 and is not part of this invention.

Figure 22:
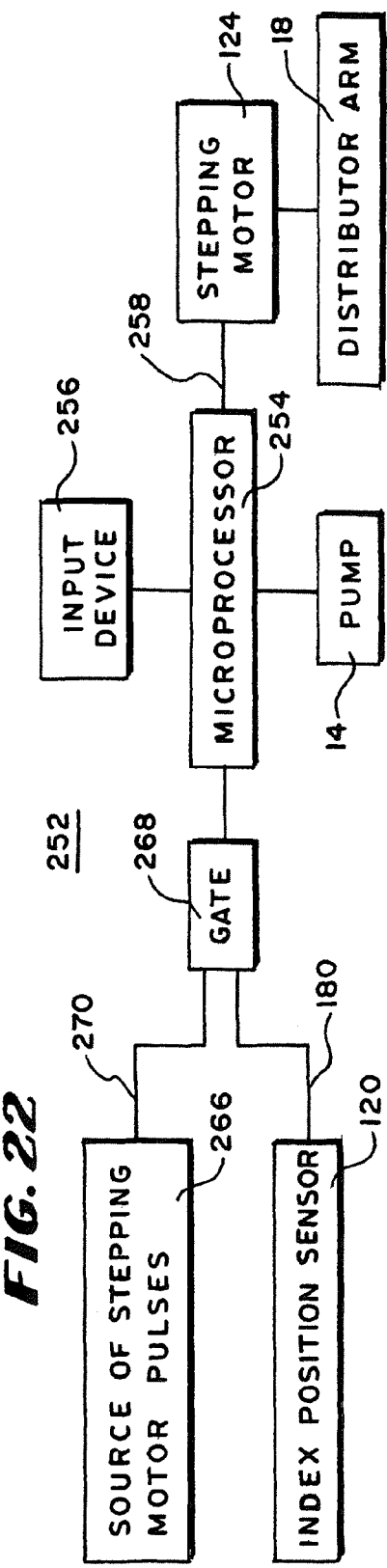
FIG. 22 is a block diagram of a portion of a control system.

In FIG. 22, there is shown a block diagram of a control system 252 having a source of stepping motor pulses 266, an index position sensor 120, a gate 268, a microcontroller 254, the stepping motor 124 and the distributor arm 18 as its principle parts. The stepping motor 124 is connected to the distributor arm 18 to drive the distributor arm from position to position. An input device 256 is connected to the microcontroller 254 for altering of a program and applying commands.

The gate 268 is connected to the index position sensor 120 through a conductor 180 so that, when the openings in the index disk are being sensed by the index position sensor 120, the gate 268 is opened. The source of stepping motor pulses 266 is connected to the gate 268 through a conductor 270 so that stepping motor pulses are applied to the microcontroller 254 resulting in the microcontroller being able to access a database to interpret the pulses as a code indicating the exact position of the index disk and distributor. With this arrangement, the microcontroller 254 may calculate the distance between the distributor arm and the direction it is to rotate and directly rotate the distributor arm over the mouth of a bottle for insertion of a sample or withdrawing of a sample as described in the aforementioned U.S. patent. In the alternative, the microcontroller 254 may activate the stepping motor 124 to return the distributor to its starting position and to begin counting to a specific bottle to be filled.

When the index disk 118 (FIG. 18) passes under a sensor to open the gate 268 to apply pulses to the microcontroller 254, the microcontroller determines if the pulses passing through the gate are in the range of the narrower slots such as 196 (FIG. 18) or wide slots such as 194 (FIG. 18). If the microcontroller recognizes a narrow slot, which is a code identification character, recognizes the next group of signals as representing a code character. Generally, the number of pulses that are applied to the microcontroller while a narrow slot is moving through the sensor may be considered as a single unit. Multiples of that number of pulses passing through the wider slots may be considered a number equivalent to the multiple so that if five times the pulses occur during the time a wide slot passes through the sensor as occur at the input the microcontroller during the time a narrow slot passes through the sensor, the code character corresponding to the wide slot may be considered a five. If there are a series of wide slots not separated by a narrow slot, a series of such code characters are generated. For example, if there are two wide slots in a row, one equal to five and the other equal to three, the microcontroller recognizes 5,3 or 3,5 as being one side or the other of a unique bottle general location corresponding to a general location on the disk and unique position on the distributor. The microcontroller than identifies a narrow slot and the distance from the narrow slot corresponding to a bottle opening and moves the bottle opening.

The reference point on the disk that positions the distributor at a location over a bottle is the trailing edge of the code identification character slot so that the resting position is recognized at the end of the traversal of a slot through the sensor. Of course, other reference points may be used instead such as one stepping motor step beyond the trailing edge and the distributor arm may be arbitrarily positioned and does not have to be aligned with any slot but may be offset a distance in accordance with the calibration of the index disk with the location of the distributor arm. While in the preferred embodiment, the microcontroller remembers the direction that the distributor arm was last moving and starts the stepping motor in that direction after motion has been terminated, other obvious algorithms may be utilized such as determining the direction by the order of the code characters on the disk or by separate indicia on the disk which point in one direction. For example, a wider slot that is distinguishable in its width from either the code character slots or the narrower marker slots followed by another slot indicating counterclockwise or a similar arrangement indicating clockwise. Moreover, more than one sensor could be used either in the same tracks or multiple tracks although the expense is increased with each sensor and each track.

Figure 23:
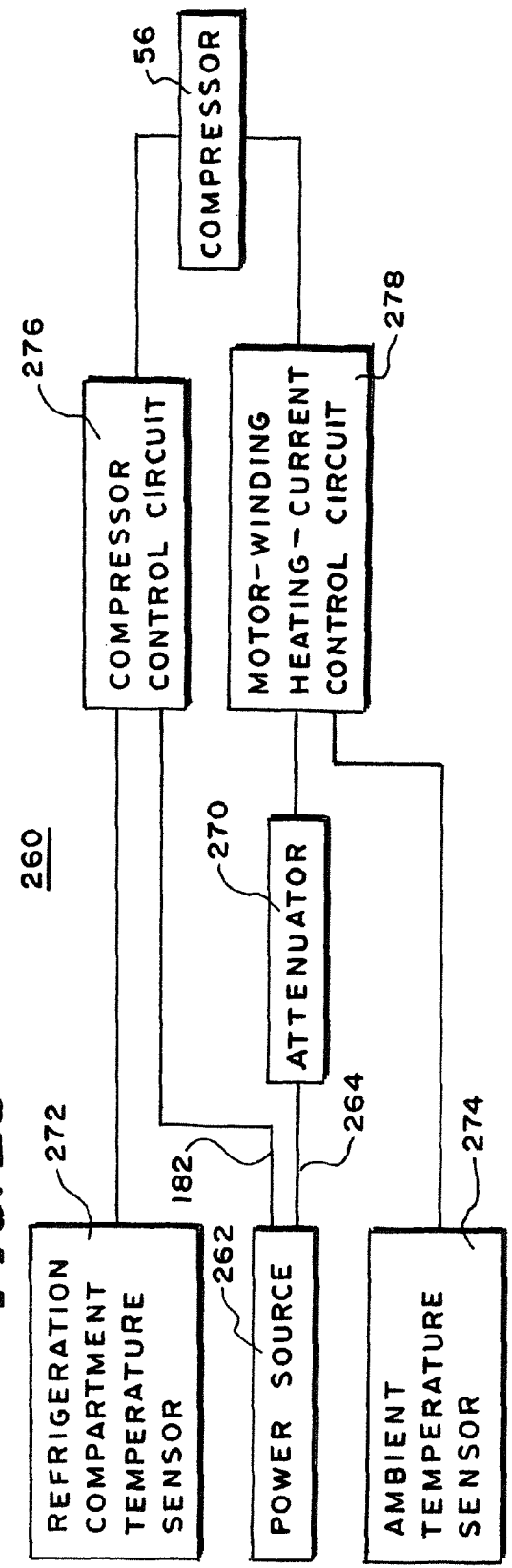
FIG. 23 is a block diagram of a heating system in accordance with an embodiment of the invention.

In FIG. 23, there is shown a system 260 for warming a compressor to a point where it may start when the ambient temperature is low. At very low ambient temperatures, if the compressor has not run for a period of time, the fluid in the refrigeration system may liquefy. If it liquefies sufficiently and collects within the compressor, it may prevent the compressor from starting. The system 260 heats the compressor without any additional external heaters or controls so as to do so at a minimum cost and nonetheless permit the compressor to be sufficiently warm for starting.

The system 260 includes a refrigeration compartment temperature sensor 272, a power source 262, an ambient temperature sensor 274, a compressor control circuit 276, a motor-winding heating-current control circuit 278 and the compressor 56. The power source 262, refrigeration compartment temperature sensor 272, compressor control circuit 276 and compressor 56 are generally part of a standard refrigeration system. In some systems, there is an ambient temperature sensor 274 as well. However, in the embodiment of FIG. 23, the compressor control circuit 276 in addition to running the compressor motor when the refrigeration compartment temperature sensor 272 indicates that the temperature in the refrigeration compartment is above the preset temperature, is also connected to the motor-winding heating-current control circuit 278 to indicate the status of the compressor motor.

The power source 262 transmits power over conductor 182 to the compressor control circuit 276 to drive the compressor 56 when the compressor control circuit 276 determines that temperature in the refrigeration compartment is too high. However, the power source 262 also supplies power to the motor-winding heating-current control circuit 278 but this power is of a nature that does not run the compressor 56 when applied to the compressor motor windings. It may be attenuated by an attenuator 270 so that the voltage is too low to start the compressor motor but other mechanisms may be utilized such as an opposing voltage or a frequency that does not operate the motor or may have any other characteristic, wave shape or form that supplies current to the windings to generate heat but does not operate the motor. The ambient temperature sensor 274 applies a signal to the motor-winding heating-current control circuit 278 and when the ambient temperature is sufficiently low to indicate a possibility that the compressor motor will not operate and the motor-winding heating-current control circuit is receiving a signal from the compressor control circuit 276 indicating that the compressor motor is not on, the motor-winding heating-current control circuit 278 applies a signal to the compressor 56 to warm the compressor 56.

While in the preferred embodiment, the heating current is applied to the field winding of a stepping motor, it could be applied to any resistive conductor in any drive mechanism.

From the above description, it can be understood that the sample collector and the components that are used in the sample collector and other apparatus have several advantages, such as: (1) they provide an economical method of forming a bottle rack; (2) they provide a superior protective coat to equipment that may be used in a corrosive environment; (3) they provide an inexpensive position sensor that indicates a unique position with simple equipment; (4) they provide an improved peristaltic pump in which a metal band utilized to close the pump is more easily positioned; (5) they provides a superior peristaltic pump tube guideway that reduces the wear on the peristaltic tube; and (6) they provide a particularly inexpensive system for maintaining a compressor sufficiently warm in a cold environment for ease of starting.

While a specific embodiment of the invention has been described with some particularity, many modifications and variations in the invention are possible within the light of the above teachings. It is therefore to be understood that within the scope of the appended claims, the invention may be practiced as specifically claimed.

What is claimed is:

1. A method of fabricating a unitary structure, comprising the steps of:
   assembling condenser coils, evaporator coils, a restrictor and support members on a unitary frame;
   powder coating the unitary frame with the condenser coils, the evaporator coils, the restrictor and the support members on it;
   mounting a compressor on the unitary frame and connecting the condenser coils and the evaporator coils to the compressor;
   sealing the connections between the compressor and the evaporator coils and the condenser coils; and
   mounting the uniform frame to an apparatus to provide a final closure.

2. The method of claim 1 in which the step of assembling condenser coils, evaporator coils, a restrictor and support members comprises the step of mounting one of an orifice restrictor and a capillary restrictor between the evaporator coils and the condenser coils.

3. The method of claim 2 in which the step of assembling the condenser coils, evaporator coils, restrictor and support members includes the steps of:
   mounting a compressor having a special protective coat on it to the unitary frame and connecting the compressor to the evaporator and condenser coils; and
   sealing the connections between the compressor and the evaporator and condenser coils with a special protective coat.

* * * * *